United States Patent [19]

Banes

[11] Patent Number: 5,518,909
[45] Date of Patent: May 21, 1996

[54] FLEXION ENHANCED TRANSFECTION OF GENETIC MATERIAL

[76] Inventor: Albert J. Banes, 1821 Coleman Loop Rd., Hillsborough, N.C. 27278

[21] Appl. No.: 342,423

[22] Filed: Nov. 18, 1994

[51] Int. Cl.$^6$ ................................................ C12N 15/64
[52] U.S. Cl. .................... 435/172.3; 435/173.6; 435/174; 435/240.2; 435/240.241
[58] Field of Search .................. 435/172.3, 240.2, 435/173, 174, 240.241

[56] References Cited

U.S. PATENT DOCUMENTS 4,789,601  12/1988  Banes ........................................ 428/447

OTHER PUBLICATIONS

*A Concise Dictionary of Biology,* 1990, Oxford University Press, Oxford, U.K., pp. 187–188.

Leung, D. Y. M. et al., "A New In Vitro System for Studying Cell Response to Mechanical Stimulations," Experimental Cell Research, 109 (1977) 285–298.

Banes, A. J. et al., "A New Vacuum–Operated Stress–Providing Instrument That Applies Static or Variable Duration Cyclic Tension or Compression to Cells In Vitro," J. Cell Sci., 1985.

Somjen, D. et al., "Bone Remodelling Induced by Physical Stress in Prostaglandin E$_2$ Mediated," Biochimica et Biophysica Acta, 627 (1980) 91–100.

Brunette, D. M. et al. "Mechanical Stretching Increases the Number of Epithelial Cells Synthesizing DNA in Culture," J. Cell Sci, 69 (1984) 35–45.

Hasagawa et al., "Mechanical Stretching Increases the Number of Cultured Bone Cells Synthesizing DNA and Alters Their Pattern of Protein Synthesis," Calcif Tissue Int. 37 (1985) 431–436.

Leung, D. Y. M. et al., "Cyclic Stretching Stimulates Synthesis of Matrix Components by Arterial Smooth Muscle Cells In Vitro," Science, 191 (1976) 475–477.

*Primary Examiner*—Mindy Fleisher
*Assistant Examiner*—James Ketter
*Attorney, Agent, or Firm*—Webb Ziesenheim Bruening Logsdon Orkin & Hanson

[57] ABSTRACT

A method of enhancing transfection of genetic material by subjecting the cells to be transfected to elongation or flexion. Preferably, the elongation or flexion is cyclical. Improved efficiency of transfection of genetic material is demonstrated in cells subjected to elongation or flexion as compared to the same transfection of the same cells under quiescent conditions. Flexion preferably takes place on a cell or cells in culture wherein the culture is adhered to a rubber-based culture well, and the rubber-based well is subjected to cyclical flexion at a rate between 100 cycles per second and 20 cycles per minute, at 0.001–25% cell elongation based on the diameter of the cell. More preferably, flexion is conducted at 60 cycles per minute for 15 minutes to 12 hours, at a maximum cellular elongation of 5–20% of the cell diameter in either a strain gradient that is maximal at the culture well periphery, minimal at the center and nominally biaxial at the periphery but up to 50% biaxial toward the well center, or is a more homogeneous biaxial load across 75% to 85% of the culture well surface.

20 Claims, No Drawings

FLEXION ENHANCED TRANSFECTION OF GENETIC MATERIAL

FIELD OF THE INVENTION

The invention relates to enhancing transfection of genetic material in cells, primarily cells in cell culture.

BACKGROUND OF THE INVENTION

The current basic understanding of gene expression has, as its source, years of cell transfection research. Early research involved introduction of genes or other defined segments of DNA into bacteria followed by assessment of the genes' ability to function normally. More recent transfection research has centered on cell life forms higher than the bacterium, and for at least several years it has been routine to introduce cloned genes into the genomes of a variety of mammalian cells.

The transfer of genes or defined segments of DNA into cells is known by a variety of synonymous terms all of which may denote either stable or transient transfer: functional DNA uptake, DNA (or gene) transmission or transfer, or DNA (or gene) transfection. Other genetic material can also be the subject of transfection, and this is known in the art. For the purposes of the following discussion and disclosure, therefore, all of these terms should be considered interchangeable.

Transfection techniques, while they are now routine, are not always as efficient as a researcher might want or need. For example, for a long time tumor virus DNA that was free of viral coat proteins was able to induce viral multiplication and give rise to progeny virus particles when it was added to susceptible host cells, rendering them cancerous. Unfortunately, the efficiency of this technique was so low it was useless for practical research. The technique became useful for basic research when it was discovered that purified DNA from adenovirus, when precipitated with $Ca^{++}$ (for example from $Ca_3(PO_4)_2$) and added to a monolayer of normal rat cells growing in culture, had a higher transfection efficiency than when $Ca^{++}$ was absent. The mechanism of the increased transfection efficiency is presumed to be a $Ca^{++}$-induced cellular phagocytosis of the infecting DNA particles, or $PO_4$ crystal-induced membrane disruption allowing DNA to enter the cytoplasm.

The above-described stimulus for transfection did not solve all transfection efficiency problems, however, because only a very small fraction of the added DNA finally became functionally integrated into the cellular DNA. Introduction of $Ca^{++}$ also affected cell biochemistry and metabolism, sometimes to an unacceptable degree.

Other transfection enhancing techniques are also well known. Diethylaminoethyl dextran (DEAE-dextran) can be used to bind genetic material such as DNA to generate a particulate DNA complex which enters host cells more readily than unbound DNA does. Another method uses polybrene, a detergent, which generates holes in the cell membranes to allow foreign genetic material to enter. Yet another method is called "lipofection", which is the inclusion of DNA or other genetic material into lipid vesicles which are inherently more able to coalesce with and cross the cell membrane to deliver genetic material to the cytoplasmic space than is the DNA itself. Finally, electrophoresis has also been used to "electroporate" the genetic material into the cells to achieve delivery and to enhance transfection. In the latter case, a brief, pulsed high voltage field creates membrane disruption and vectorially drives genetic material through the plasma membrane into the cytoplasmic space. Alternatively, the genetic material may enter the cell after electroporation by diffusion.

The DEAE-dextran, polybrene, lipofection, electroporation, $Ca^{++}$ and other techniques all share the same general disadvantages: the ions or other substances, or the electricity, may well enhance transfection but also have greater or lesser deleterious effects on cell morphology or metabolism. Electroporation, in particular, can be fatal to cells due to generation of unwanted heat. These techniques rely on creating holes in the plasma membrane of target cells so that particulate DNA may enter by diffusion or, in the case of lipofection, so that the membranes of genetic material containing vesicles will merge with the target cell plasma membrane to achieve cellular uptake. These techniques do not stimulate phagocytosis by the target cells as a method to increase the efficiency of DNA uptake.

Accordingly, a need thus remains for a transfection enhancement method which is widely applicable and highly effective and, preferably, is biochemically and electrically neutral.

SUMMARY OF THE INVENTION

In order to meet this need, I have developed a method of enhancing transfection of genetic material by subjecting the cells to be transfected to cyclic mechanical deformation, or flexion. Flexion, or flexing, stretches the cells and elongates them. Preferably, the flexion is cyclical. Improved efficiency of transfection of DNA and other genetic material has been demonstrated in cells subjected to flexion as compared to the same transfection of the same cells under quiescent conditions.

DETAILED DESCRIPTION OF THE INVENTION

The present method enhances transfection of genetic material by flexing, usually cyclically, the cells to be transfected. The flexing of the cells is generally an elongation of the cells or any application of tensile or shear stress, or compression or inertial loading or fluid movement, to the cell wall(s). Flexion and elongation are similar, except that the flexion is the application of force to the cell and elongation is the result of the force application to the cell. Improved efficiency of transfection has been demonstrated in cells subjected to flexion/elongation as compared to the same transfection of the same cells under non-flexion conditions.

Actual flexing of cells has been amply described in prior art publications and patents. One system for the in vitro flexing of cells in culture is documented in Banes, A. J., et al., "A New Vacuum-Operated Stress-Providing Instrument that Applies Static or Variable Duration Cyclic Tension or Compression to Cells In Vitro," *J. Cell Sci.*, 1985. Related in vitro systems are documented in Somjen, D., et al., "Bone Remodelling Induced by Physical Stress in Prostaglandin $E_2$ Mediation," *Biochimica et Biophysica Acta*, 627 (1980) 91–100; Leung, D. Y. M. et al., "A New In Vitro System for Studying Cell Response to Mechanical Stimulation," *Experimental cell Research*, 109 (1977) 285–298; Leung, D. Y. M. et al., "Cyclic Stretching Stimulates Synthesis of Matrix Components by Arterial Smooth Muscle Cells In Vitro," *Science*, 191 (1976) 475–477; Hasagawa et al., "Mechanical Stretching Increases the Number of Cultured Bone Cells Synthesizing DNA and Alters their Pattern of Protein Synthesis," *Calcif. Tissue Int*, 37 (1985) 431–436;

and Brunette, D. M. et al., "Mechanical Stretching Increases the Number of Epithelial Cells Synthesizing DNA in Culture," *J. Cell. Sci.*, 69 (1984) 35–45. More recently, a family of patents has issued to the present inventor, all with identical specifications and including disclosures regarding cell flexion systems and biocompatible polymeric surfaces suitable for cell culture adherence. U.S. Pat. No. 4,789,601 is exemplary and is incorporated herein by reference.

By applying flexion to cells into which transfection of genetic material is intended, the flexion increases the efficiency of the transfection as compared with the same transfection protocol conducted without flexion. In theory, although the Applicant does not intend to be bound by this theory, it is believed that the flexion temporarily alters either the structure of the cell membrane, the cell matrix-integrin cytoskeleton, the activity of the plasma membrane enzymes, or all of these, so as to increase the endocytosis, phagocytosis, pinocytosis or ability of the plasma membrane to form vesicles, undergo membrane fusion and engulf them. The latter process may enhance uptake of exogenous genetic material and accelerate transfection or incorporation of the genetic material into the host DNA. Flexion of cells stimulates DNA synthesis and therefore may provide a host cell that more actively incorporates foreign DNA. Uptake of the genetic material is commensurately enhanced. Flexion cycles between about 100 times per second and about 20 times per minute are contemplated, with preferred flexion rates being about 60 times per minute (one cycle per second, or 1 Hz) for 15 minutes to 12 hours. Actual cell elongation should vary between 0.0001 and 25% preferably between about 0.01–20% and most, preferably 5–20%. Percent elongation being defined as $\Delta l/l \times 100\%$ wherein l equals initial cell length and $\Delta l$ equals extended cell length minus initial cell length. The flexion applies strain to the cells, and the applied strain may be either a radial strain gradient that is maximal at the culture well periphery and minimal at the well center, having a nominal circumferential strain at the periphery but about 30% circumferential strain at the center in a thick membrane (2.7 mm thick, 25 mm diameter). Alternatively, membrane strain may be a more relatively homogeneous radial strain (75–85% homogeneous) across the well surface and biaxial with circumferential strain decreasing from the well center to the edge in a thin membrane embodiment (BiFlex membrane 0.020" thick). Alternatively, strain may be relatively homogeneous in the radial direction with little circumferential strain.

The details of the particular flexion technique employed may vary. Cells to be transfected can be plated on a flexible bottomed culture plate, and cyclically stretched and contacted with genetic material, either immediately or after 1–48 hours, by dispersing the genetic material into the medium overlaying the cell culture. Standard cell culture medium should be used, and media suitable for use during transfections is well known in the art. After addition of the genetic material to the medium, the cells should be flexed and incubated in the presence of the genetic material for about 24–48 hours. This is the time frame during which flexion enhances uptake of genetic matter as well as stimulates DNA synthesis. Alternatively, the cells can be plated, flexed and contacted with the genetic material but also subjected to controlled amounts of chemically or electrophoretically driven transfection enhancements. Another option is to mix cells and genetic material prior to plating and flexion, for example by trypsinizing the cells and mixing them with DNA and a transfection agent, then plating and flexing the cells. The use of flexion still ameliorates the unwanted effects of these adjunct processes by minimizing the extent to which they are necessary. Application of an electric field or current in the form of electroporation may be used in conjunction with flexion, and can be implemented either with electrodes fitted at the top and bottom of the cell culture wells or with an electrically conductive material incorporated into the rubber well base.

As a general rule, if flexion and an alternative transfection enhancement method (such as DEAE-dextran, polybrene, lipofection, electroporation, etc.) are used in the same protocol, the flexion should precede the alternative transfection enhancement method and should stop before its initiation. For example, flexion plus calcium phosphate addition together encourage the unwanted detachment of the cell culture from the cell culture surface. Therefore, $Ca_3(PO_4)_2$ should be added directly after flexion.

The following example of DNA transfection using the present invention is illustrative.

EXAMPLE 1

A well-known DNA transfection exercise is repeated, but in addition to the known protocol the cells in culture are cyclically flexed. Tk⁻ (thymidine kinase) mouse cells are plated onto biocompatible rubber well surfaces and contacted with DNA containing the thymidine kinase gene from herpes simplex virus, in a cell culture medium non-toxic to Tk⁻ mouse cells. The cell culture is flexed at 1 cycle per second for 12 hours. To assay for successful transfection, HAT (hypoxanthine, aminopterin, thymidine) medium is added to the cell cultures. Because HAT is toxic to Tk⁻ mouse cells, after a further incubation period of 48 hours any surviving mouse cells will have been successfully transfected with the thymidine kinase gene.

Despite the particular description above and in the illustrative Example, the invention is intended to be limited only insofar as is set forth in the accompanying claims.

I claim:

1. A method for enhancing transfection of genetic material into a eukaryotic cell, comprising the step of flexing a eukaryotic cell in conjunction with effecting transfection in said cell.

2. The method according to claim 1 wherein said flexing step includes cyclic flexing conducted between 100 times per second and 20 times per minute.

3. The method according to claim 1 wherein said flexing step includes cyclic flexing at a rate of about 60 times per minute.

4. The method according to claim 1 wherein said flexing step is conducted first, and a quantity of genetic material to be transfected into said cell is subsequently delivered to said cell.

5. The method according to claim 1 wherein said flexing step is conducted simultaneously with contacting of a quantity of genetic material onto said cell.

6. The method according to claim 1 wherein said flexing step includes flexing said cell, said cell having an initial cell length, to yield a cell elongation between 0.0001 and 25% of the longest dimension of said cell resulting in a corresponding extended cell length, with elongation being defined as $\Delta l/l \times 100\%$ where l equals said initial cell length and $\Delta l$ equals said extended cell length minus said initial cell length.

7. The method according to claim 1 wherein said flexing step includes flexing said cell at a cell elongation between 0.01 and 20% of the longest dimension of said cell, wherein said dimension is either the diameter or length of said cell.

8. The method according to claim 1 further including the step of plating said cell onto a flexible culture well prior to flexing and contacting said cell with a quantity of cell culture medium.

9. The method according to claim 1 wherein said flexing step is conducted first and a quantity of DNA to be transfected into said cell is subsequently delivered to said cell together with an additional substance selected from the group consisting of calcium ion, diethylaminoethyl dextran, polybrene and lipid in the form of DNA included in liposomes.

10. The method according to claim 1 wherein said flexing step is conducted first and a quantity of DNA to be transfected into said cell is subsequently contacted onto said cell together with the application of an electric current.

11. A method for enhancing transfection of genetic materials into a quantity of eukaryotic cells in culture, comprising the steps of:

plating a eukaryotic host cell for transfection on a flexible cell culture well of a rubber-based compound;

overlaying a quantity of cell culture medium in said flexible cell culture well;

flexing said flexible cell culture well between 100 times per second and 20 times per minute; and contacting said cell culture medium with genetic material during the flexing step.

12. The method according to claim 11 wherein said flexing includes flexing said flexible cell culture well at about 60 times per minute.

13. The method according to claim 12 further including the step of adding to said well, after the genetic material contacting step, an additional substance selected from the group consisting of calcium ion, diethylaminoethyl dextran, polybrene and lipid.

14. The method according to claim 12 further including the step of creating, after the genetic material contacting step, an electric field in the area of said flexible cell culture well.

15. The method according to claim 14 wherein during said flexing step said cells are elongated by between about 0.01–20%.

16. A method for enhancing transfection of genetic material into a quantity of eukaryotic cells in culture, comprising the steps of:

plating a eukaryotic host cell for transfection on a flexible cell culture well of a rubber-based compound;

overlaying a quantity of cell culture medium in said flexible cell culture well;

flexing said flexible cell culture well between 100 times per second and 20 times per minute; and contacting said cell culture medium with genetic material after the flexing step.

17. The method according to claim 16 wherein said flexing step includes flexing said flexible cell culture well at about 60 times per minute.

18. The method according to claim 17 further including the step of adding to said well, after the genetic material contacting step, an additional substance selected from the group consisting of calcium ion, diethylaminoethyl dextran, polybrene and lipid.

19. The method according to claim 17 further including the step of creating, after the genetic material contacting step, an electric field in the area of said flexible cell culture well.

20. The method according to claim 19 wherein during said flexing step said cells are elongated by between about 5–20%.

* * * * *